(12) United States Patent
Park et al.

(10) Patent No.: US 10,585,039 B1
(45) Date of Patent: Mar. 10, 2020

(54) OPTICAL DETECTION SYSTEM

(71) Applicants: THE WAVE TALK, INC., Daejeon (KR); Korea Advanced Institute of Science and Technology, Daejeon (KR)

(72) Inventors: Hui Jun Park, Daejeon (KR); Kyeo Reh Lee, Chungcheongnam-do (KR); Seung Woo Shin, Busan (KR); YongKeun Park, Daejeon (KR)

(73) Assignees: THE WAVE TALK, INC., Daejeon (KR); Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 16/184,677

(22) Filed: Nov. 8, 2018

(30) Foreign Application Priority Data

Sep. 7, 2018 (KR) .......................... 10-2018-0107292

(51) Int. Cl.
*G01N 21/00* (2006.01)
*G01N 21/51* (2006.01)
*G01N 21/94* (2006.01)

(52) U.S. Cl.
CPC ............. *G01N 21/51* (2013.01); *G01N 21/94* (2013.01); *G01N 2201/0675* (2013.01)

(58) Field of Classification Search
CPC . G01N 21/51; G01N 21/94; G01N 2201/0675
USPC ........................................................ 356/341
See application file for complete search history.

(56) References Cited

U.S. PATENT DOCUMENTS

| | | | |
|---|---|---|---|
| 2012/0086948 A1 | 4/2012 | Song | |
| 2014/0107944 A1* | 4/2014 | Ben-Amotz | G01N 21/65 702/30 |
| 2015/0241342 A1* | 8/2015 | Zhou | G01N 15/1425 356/432 |
| 2017/0123197 A1* | 5/2017 | Reuss | G02B 21/0032 |
| 2018/0348496 A1* | 12/2018 | Brown | G01N 21/6458 |

FOREIGN PATENT DOCUMENTS

| | | |
|---|---|---|
| KR | 10-2012-0036727 A | 4/2012 |
| KR | 10-2018-0053984 A | 5/2018 |

OTHER PUBLICATIONS

Korean Office Action with translation of Korean Patent Application No. 10-2018-0107292 dated Dec. 10, 2019.

* cited by examiner

*Primary Examiner* — Sunghee Y Gray
(74) *Attorney, Agent, or Firm* — Marshall, Gerstein & Borun LLP

(57) ABSTRACT

An optical detection system includes a sample portion accommodating a sample, a wave source emitting waves to the sample portion, an optical portion provided on a path of an output wave output from the sample portion, and comprising a first spatial light modulator that modulates part of the output wave to a first wave and a second spatial light modulator that modulates part of the output wave to a second wave, a lens portion focusing the first wave and the second wave output from the optical portion, and a detection portion detecting a focused wave that is focused by the lens portion, in which the first spatial light modulator and the second spatial light modulator modulate the output wave such that the first wave and the second wave have destructive interference with respect to the sample under an already known condition.

4 Claims, 6 Drawing Sheets

OPTICAL DETECTION SYSTEM

CROSS-REFERENCE TO RELATED APPLICATION

This application claims the benefit of Korean Patent Application No. 10-2018-0107292, filed on Sep. 7, 2018, in the Korean Intellectual Property Office, the disclosure of which is incorporated herein in its entirety by reference.

BACKGROUND

1. Field

One or more embodiments relate to an optical detection system.

2. Description of the Related Art

Unintended generation of microorganisms in a manufacturing process has frequently occurred in the field of food production. To check microbial growth, a method of counting culture types using a medium has been used as a cell detection system. For example, as a microorganism counting method, a method of counting the number of colonies of microorganisms cultured by using an agar medium is used. Instead of a method of visually counting the number of colonies generated in the agar medium, recently, a method of counting the number of colonies by processing data of an image of a medium whose colonies are to be counted, the image being captured by using a charge-coupled device (CCD) camera, has been suggested.

However, since the above counting methods cannot directly count the population of microorganisms and only can count the number of microorganisms by culturing a microorganism to a colony state in which the microorganisms are visible to the naked eye, at least one day is required for counting.

SUMMARY

One or more embodiments include an optical detection system which may detect, in real time, impurities such as microorganism in a sample.

Additional aspects will be set forth in part in the description which follows and, in part, will be apparent from the description, or may be learned by practice of the presented embodiments.

According to one or more embodiments, an optical detection system includes a sample portion accommodating a sample, a wave source emitting waves to the sample portion, an optical portion provided on a path of an output wave output from the sample portion, and including a first spatial light modulator that modulates part of the output wave to a first wave and a second spatial light modulator that modulates part of the output wave to a second wave, a lens portion focusing the first wave and the second wave output from the optical portion, and a detection portion detecting a focused wave that is focused by the lens portion, in which the first spatial light modulator and the second spatial light modulator modulate the output wave such that the first wave and the second wave have destructive interference with respect to the sample under an already known condition.

The output wave may include a speckle pattern that is generated by being multiple-scattered from the sample.

The sample portion may further include a multiple scattering amplification portion that amplifies a number of multiple scattering of the waves emitted to the sample.

The detection portion may detect the existence of impurities in the sample according to detection of the presence of the focused wave.

According to one or more embodiments, an optical detection system includes a sample portion accommodating a sample, a wave source emitting waves to the sample portion, an optical portion provided on a path of an output wave output from the sample portion, and including a first spatial light modulator that modulates part of the output wave to a first wave, a lens portion focusing the first wave output from the optical portion and a second wave that is part of the output wave, and a detection portion detecting a focused wave that is focused by the lens portion, in which the first spatial light modulator modulates the output wave such that the first wave and the second wave have destructive interference with respect to the sample under an already known condition.

The output wave may include a speckle pattern that is generated by being multiple-scattered from the sample.

The sample portion may further include a multiple scattering amplification portion that amplifies a number of multiple scattering of the waves emitted to the sample.

The detection portion may detect the existence of impurities in the sample according to detection of the presence of the focused wave.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
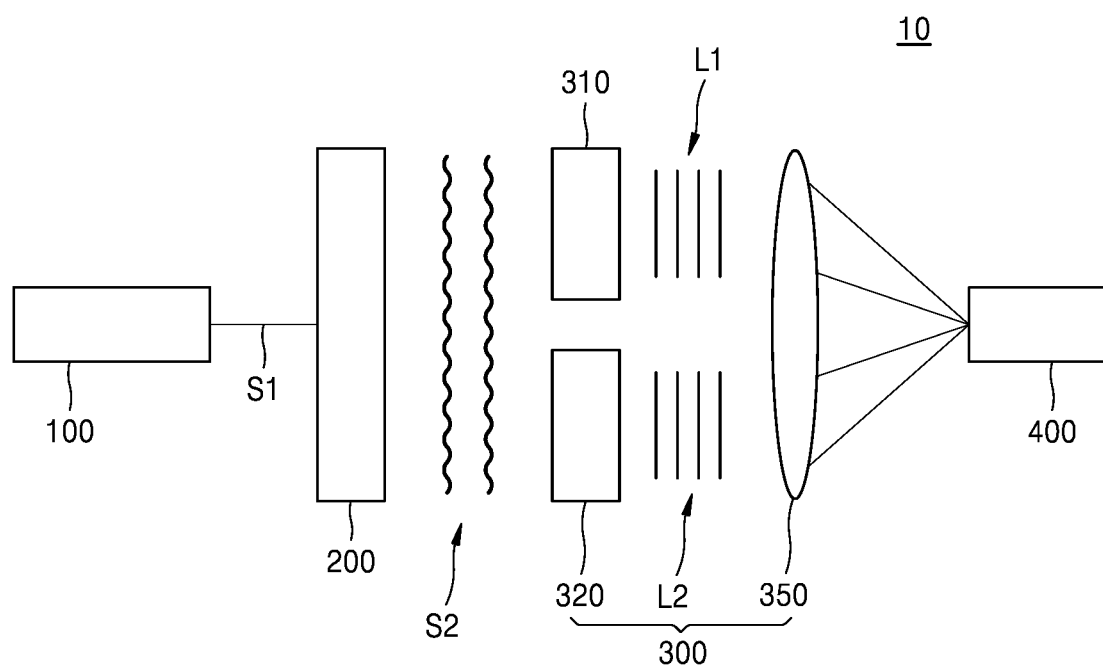
FIG. 1 is a schematic diagram of an optical detection system according to an embodiment.

Hereinafter, the present disclosure will be described in detail by explaining embodiments of the disclosure with reference to the attached drawings. Like reference numerals in the drawings denote like elements, and redundant descriptions thereof are omitted.

The present disclosure will now be described more fully with reference to the accompanying drawings, in which embodiments of the disclosure are shown. The disclosure may, however, be embodied in many different forms and should not be construed as being limited to the embodiments set forth herein; rather, these embodiments are provided so that this disclosure will be thorough and complete, and will fully convey the concept of the disclosure to those of ordinary skill in the art.

It will be understood that although the terms "first," "second," etc. may be used herein to describe various components, these components should not be limited by these terms. These components are only used to distinguish one component from another.

As used herein, the singular forms "a," "an" and "the" are intended to include the plural forms as well, unless the context clearly indicates otherwise.

It will be understood that the terms "comprises" and/or "comprising" used herein specify the presence of stated features or components, but do not preclude the presence or addition of one or more other features or components.

It will be further understood that when a unit, area, or component is referred to as being "formed on" another unit, area, or component, it can be directly or indirectly formed on the other unit, area, or component. That is, for example, intervening units, areas, or components may be present.

It will be further understood that the terms "connect" and/or "combine" used herein, unless the context clearly indicates otherwise, do not necessarily intend direct and/or fixed connection or combination of two members, and are not intended to preclude the possibility of other intervening member between the two members.

Sizes of components in the drawings may be exaggerated for convenience of explanation. In other words, since sizes and thicknesses of components in the drawings are arbitrarily illustrated for convenience of explanation, the following embodiments are not limited thereto.

FIG. 1 is a schematic diagram of an optical detection system 10 according to an embodiment.

Referring to FIG. 1, the optical detection system 10 according to an embodiment may include a wave source 100, a sample portion 200, an optical portion 300, and a detection portion 400.

The wave source 100 may include all types of source devices capable of generating waves, for example, a laser that emits light of a specific wavelength band. The wave source 100 is connected to a driving device such as a motor or an actuator, and may sequentially emit waves toward the sample portion 200 at a preset time interval. Although the present disclosure is not limited to the type of a wave source, however, in the following description, for convenience of explanation, a case in which the wave source 100 is a laser is mainly described.

For example, in order to form a speckle in a sample S accommodated in the sample portion 200, a laser with excellent coherence may be used as the wave source 100. In this state, measurement accuracy may increase as a spectral bandwidth of a wave source that determines the coherence of a laser wave source decreases. In other words, the measurement accuracy may increase as a coherence length increases. Accordingly, laser light having a spectral bandwidth of a wave source that is less than predefined reference bandwidth may be used as the wave source 100. As the spectral bandwidth of a wave source is shorter than the reference bandwidth, the measurement accuracy may increase. For example, the spectral bandwidth of the wave source 100 may be set such that the condition of Inequality 1 below may be maintained.

Spectral bandwidth<1 nm [Inequality 1]

According to Inequality 1, when light is emitted to the sample portion 200 at each reference time to measure a pattern change of a laser speckle, the spectral bandwidth of the wave source 100 may be maintained less than 1 nm.

Figure 2:
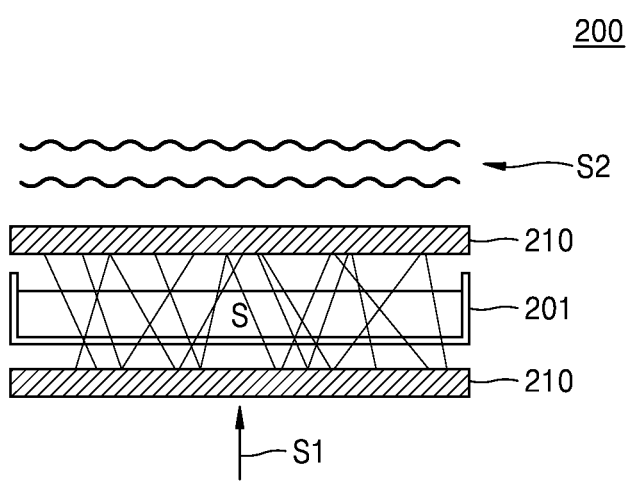
FIGS. 2 and 3 are schematic diagrams of a sample portion of the optical detection system of FIG. 1.
Figure 3:
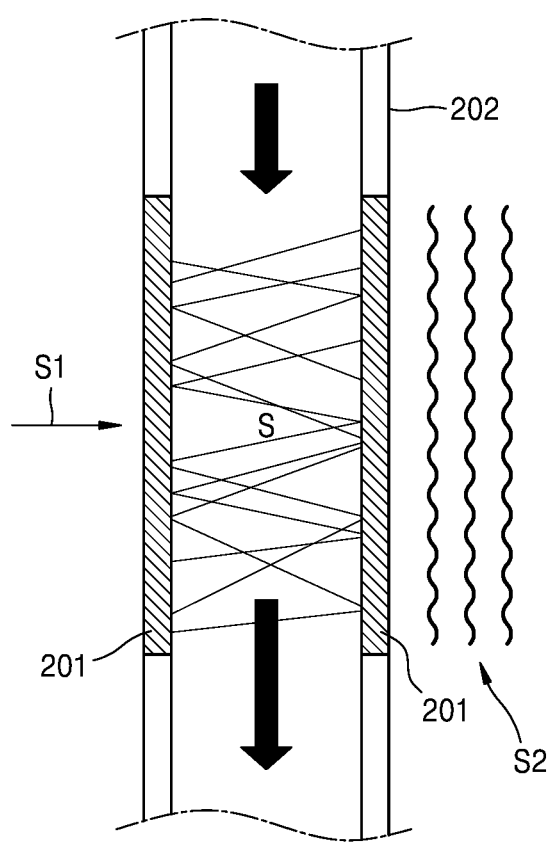

FIGS. 2 and 3 are schematic diagrams of the sample portion 200 of the optical detection system 10 of FIG. 1.

Referring to FIGS. 1 to 3, the sample portion 200 may accommodate the sample S to be measured. The sample S may be accommodated by means of a sample arrangement device such as a container 201 or a pipe 202, and may be accommodate in a static state. In an embodiment, as illustrated in FIG. 2, the sample portion 200 may accommodate the sample S that is static without fluidity, by using the container 201. In another embodiment, as illustrated in FIG. 3, the sample portion 200 may accommodate the sample having fluidity, by using the pipe 202. In this state, the sample S may be liquid, and the sample portion 200 circulates the sample S at least one time along an entire flow path including the pipe 202, thereby forming a static state of the sample S in the pipe 202.

The sample portion 200 may further include a multiple scattering amplification portion 210. The multiple scattering amplification portion 210 may amplify the frequency of multiple scattering in the sample S by reflecting at least part of the waves output from the sample S toward the sample S. The multiple scattering amplification portion 210 may include a multiple scattering material. For example, the multiple scattering material may include titanium oxide ($TiO_2$), and the multiple scattering amplification portion 210 may reflect at least part of the waves input to the multiple scattering amplification portion 210. The multiple scattering amplification portion 210 may be disposed adjacent to the sample S, and the waves emitted by being multiple-scattered from the sample S may reciprocate at least one time in a space between the sample S and the multiple scattering amplification portion 210. The multiple scattering amplification portion 210 may be disposed on a path of the waves at a position adjacent to an input wave S1 and an output wave S2.

In another embodiment, the optical detection system 10 may be configured such that the multiple scattering material is included in the sample S. The sample portion 200 may include a multiple scattering amplification area 210 in a main body of the pipe 202. The multiple scattering amplification area 210 may scatter into the sample S again at least part of the waves that is input to an inner space of the pipe 202, passes through the sample S, and is output. The waves scattered as above may be output to the other side by passing through a fluid, and then scattered. The frequency of multiple scattering may be increased in the fluid through the above process. The multiple scattering amplification area 210 may be formed in at least a partial area of a path through which the waves pass or, for example, in an entire area thereof.

The optical portion 300 may transmit the output wave S2 to the detection portion 400 by controlling a wave front of the output wave S2. In detail, the optical portion 300 may include one or more spatial light modulators (SLMs) and a lens portion 350 that focuses the waves output from the SLMs and transmits the focused waves to the detection portion 400.

The SLMs 310 and 320 may control wave fronts of the waves scattered by the sample S and provide the controlled waves to the lens portion 350. The SLMs 310 and 320 may be referred to as the wave shaping devices. The SLMs 310 and 320 may modulate the intensity of waves, or simultaneously modulate the intensity and phase of waves. The SLMs 310 and 320 may include a mechanism or an apparatus, such as a liquid crystal spatial light modulator (LC-SLM), a digital micromirror device (DMD), a deformable mirror (DM), which is capable of controlling the wave front in a desired shape in unit of pixels.

In the optical detection system 10 according to an embodiment, the SLMs 310 and 320 may include the first SLM 310 and the the second SLM 320. In this state, the first SLM 310 and the second SLM 320 may be arranged not to overlap each other on a path on which the output wave S2 output from the sample portion 200 passes. The first SLM 310 and the second SLM 320 may control, at their respective positions, the wave front of the output wave S2.

The first SLM 310 and the second SLM 320 may control the output wave S2 output from the sample S in a static state so that the controlled wave front may have preset wave front information.

A method of detecting an object such as foreign materials or impurities by controlling the wave front at the optical portion 300 is described with reference to FIG. 4.

Figure 4:
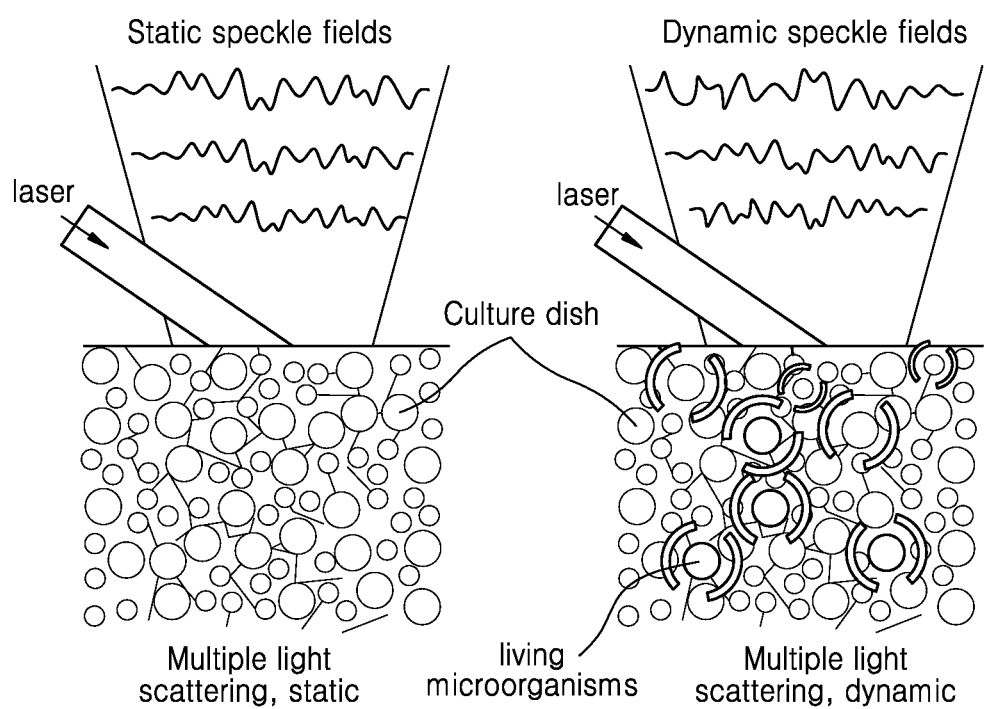
FIG. 4 is a view showing a principle of generation of a speckle pattern including sample information.
Figure 5A:
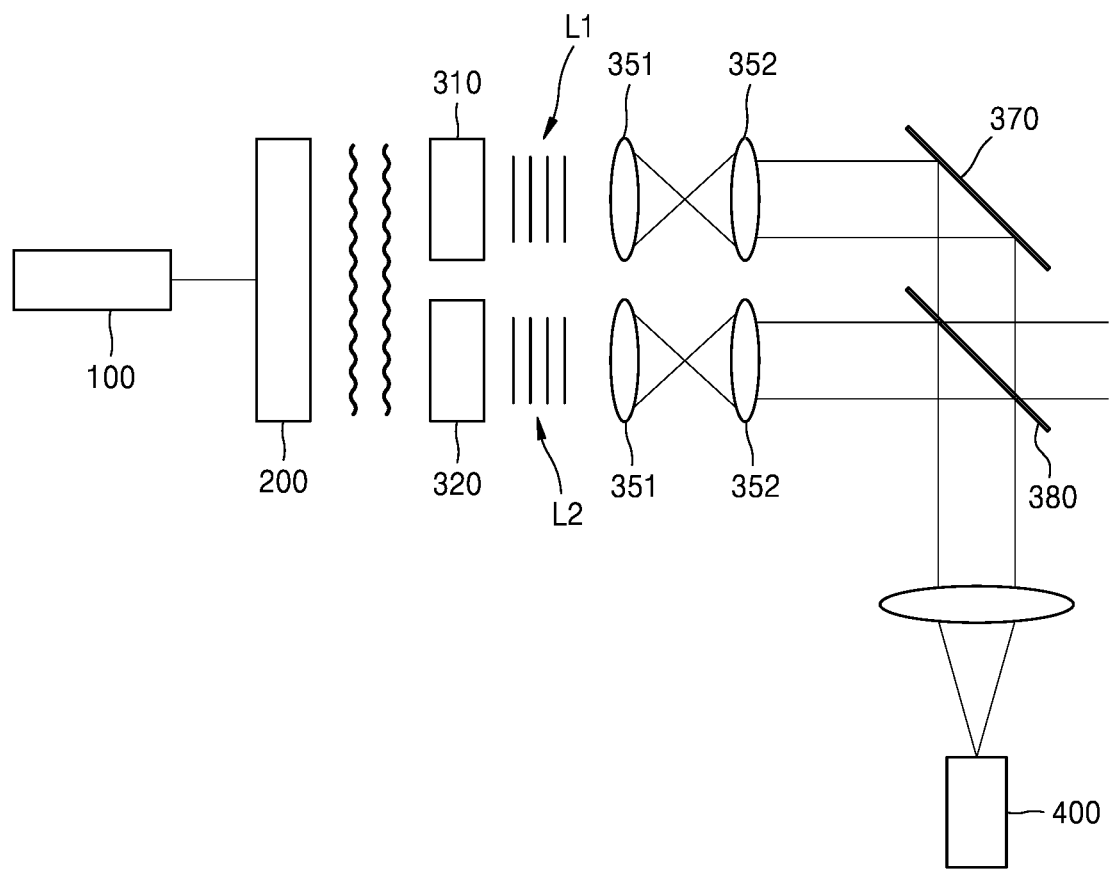
FIGS. 5A and 5B are schematic diagrams showing a principle of detection of an object by using an optical detection system according to an embodiment.
Figure 5B:
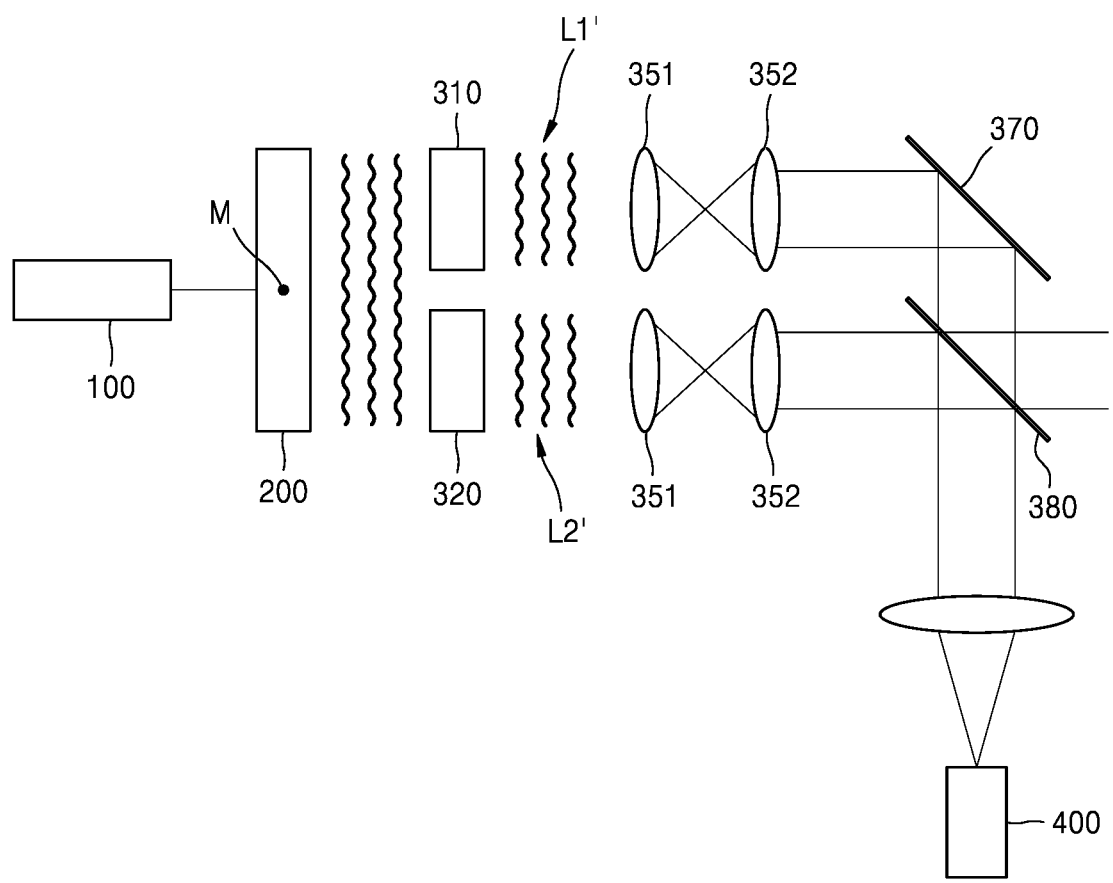

FIG. 4 is a view showing a principle of generation of a speckle pattern including sample information. FIGS. 5A and 5B are schematic diagrams showing a principle of detection of an object M by using the optical detection system 10, according to an embodiment.

Referring to FIG. 4, part of waves of the input wave S1 emitted from the wave source 100, which is scattered in complicated paths through the multiple scattering of the sample portion 200, passes through a test target surface. The waves that pass through many points on the test target surface generate constructive interference or destructive interference, and the constructive/destructive interference of the waves generates a grainy pattern, that is, a speckle pattern. In this state, when the sample S is in a static state in which there is no movement in an inner constituent material, and interference light, for example, laser light, is irradiated, a stable speckle pattern may be observed. However, when the inner constituent material includes any moving unstable medium such as foreign materials or impurities, for example, bacteria, or when the static state is broken as foreign materials or impurities are generated, the speckle pattern is changed. In other words, the output wave S2 that passes through the sample portion 200 may include sample information according to the speckle pattern.

Referring to FIG. 5A, when the sample S is in a static state in which there is no movement of the inner constituent material, the first SLM 310 and the second SLM 320 may control wave front so that the output wave S2 output from the sample portion 200 has preset intensity and phase. The first SLM 310 may control the output wave S2 with a first wave L1 having first wave information, and the second SLM 320 may control the output wave S2 with a second wave L2 having second wave information. In this state, in an embodiment, the first wave information and the second wave information may have the same intensity of waves, but have opposite wave phases. This may be summarized by Inequality 2 below.

$$I(L1) = I(L2)$$

$$P(L1) = P(L2) + \pi \quad \text{[Inequality 2]}$$

In Inequality 2, "I" denotes the intensity of waves, and "P" denotes the phase of waves. Accordingly, when the sample S is in the static state and the first wave L1 and the second wave L2 are focused by the lens portion 350, since the intensity is the same, but the phase are opposite, destructive interference may occur, and thus ideally the detection portion 400 may not detect light as in Inequality 3.

$$I(L1+L2) = 0 \quad \text{[Inequality 3]}$$

Referring to FIG. 5B, when the object M such as foreign materials or impurities is included in the sample S, the speckle pattern of the output wave S2 output from the sample portion 200 is changed. in the state in which the wave front is controlled by the above configuration, when the output wave S2 having the changed speckle pattern is incident on to the first SLM 310 and the second SLM 320, the output wave S2 is not controlled to have preset wave information. In other words, in a changed first wave L' and a changed second wave L', the intensity is not the same and the phases are not opposite to each other. Accordingly, the detection portion 400 may detect light having certain intensity as in Inequality 4, unlike Inequality 3.

$$I(L1'+L2') = kx \quad \text{[Inequality 4]}$$

In Inequality 4, "k" denotes an amplification constant in the detection portion 400.

The lens portion 350 may focus the first wave L1 and the second wave L2 respectively output from the first SLM 310 and the second SLM 320, and provide the focused waves to the detection portion 400. In this state, the lens portion 350 may include a single lens as shown in FIG. 1, and include a plurality of lenses 351 and 352, arranged on respective paths as shown in FIGS. 5A and 5B. The lens portion 350 may further include optical path means such as a mirror 370 or a beam splitter 380 to change optical paths of the first wave L1 and the second wave L2.

In another embodiment, when the sample S is in the static state, the intensities of the first wave L1 and the second wave L2 controlled by the first SLM 310 and the second SLM 320 may be different from each other. As illustrated in FIG. 5A or FIG. 5B, as the second wave L2 output from the second SLM 320 is divided by the beam splitter 380, the intensity provided to the detection portion 400 may be less than that of the first wave L1. To be offset at the detection portion 400, the first SLM 310 may control the first wave L1 such that the intensity of the first wave L1 is identical to the intensity of the second wave L2 that passes through the beam splitter 380 and is provided to the detection portion 400. Accordingly, before being controlled the first SLM 310 and the second SLM 320 and input to the lens portion 350, the intensities of the first wave L1 and the second wave L2 may be different from each other.

The detection portion 400 may detect a focused wave that is output from the optical portion 300 and then focused. The detection portion 400 may be any means to detect waves. For example, the detection portion 400 may be a photodiode. As described above, the first wave L1 and the second wave L2 output from the optical portion 300 are not detected by the detection portion 400 due to the destructive interference, but when the object M such as foreign materials or impurities is included in the sample S, waves (light) may be directly detected.

In another embodiment, the detection portion 400 may further include an optical fiber, and may receive the first wave L1 and the second wave L2 from the optical portion 300. The optical fiber may be a single mode fiber. As the first wave L1 and the second wave L2 pass through a single mode fiber, single mode filtering may be performed. Instead of the single mode fiber, a small pinhole having a size less than or equal to a size of a single mode light focus may be used.

Figure 6:
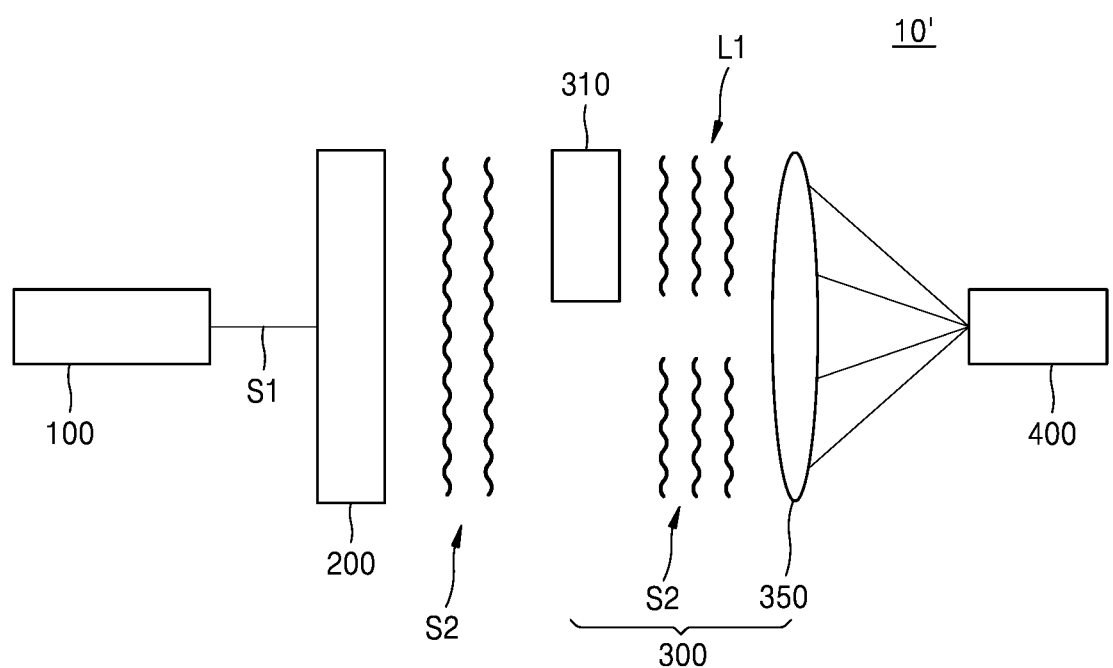
FIG. 6 is a schematic diagram of an optical detection system according to another embodiment.

FIG. 6 is a schematic diagram of an optical detection system 10' according to another embodiment.

Referring to FIG. 6, the optical detection system 10' according to another embodiment may include the wave source 100, the sample portion 200, the optical portion 300, and the detection portion 400. Since the constituent elements of the optical detection system 10' according to the present embodiment are the same as those of the optical detection system 10, except the optical portion 300, descriptions thereof are omitted for convenience of explanation.

According to the present embodiment, the optical portion 300 may include the first SLM 310 only. The first SLM 310 may convert the output wave S2 to the first wave L1 by controlling the output wave S2. In this state, the optical portion 300 may provide part of the output wave S2, without change, as the second wave L2, to the lens portion 350. In other words, the optical portion 300 may use part of the output wave S2 as the second wave L2, and control the other part thereof to have destructive interference with the second wave L2, thereby performing the same function in the above-described embodiment.

As described above, in the optical detection systems according to the above-described embodiments, since the waves output from a sample is divided into two of a first wave and a second wave, the intensity and phase of at least one of the first wave and second wave may be controlled by using the SLM such that and the first wave and the second wave have destructive interference in the detection portion 400. Through the process, in the optical detection systems according to the above-described embodiments, existence of impurities such as microorganisms in the sample may be detected only by detecting the presence of waves in the detection portion. Furthermore, in the optical detection systems according to the above-described embodiments, since the existence of impurities may be directly identified through the presence of waves, sensitive detection may be possible even when a very small amount of impurities exists.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. An optical detection system comprising:
    means for accommodating a sample, said sample accommodating means including one of a group including a container and a pipe, accommodating a sample to be subjected to optical detection;
    a wave source emitting waves to the sample in the sample accommodating means;
    a system of one or more spatial light modulators provided on a path of an output wave output from the sample in the sample accommodating means, and comprising a first spatial light modulator that controls a wave front of a first output wave to produce a first wave shape and a second spatial light modulator that controls a wave front of a second output wave to produce a second wave shape;
    a lens portion focusing the first wave and the second wave output from the optical portion; and
    means to detect waves, said means including a photodiode, detecting a focused wave that is focused by the lens portion,
    wherein, in controlling the respective wave front of the first output wave and the second output wave, the first spatial light modulator and the second spatial light modulator result in the first wave and the second wave having destructive interference with respect to the sample under an already known condition.

2. The optical detection system of claim 1, wherein the output wave comprises a speckle pattern that is generated by being multiple-scattered from the sample.

3. The optical detection system of claim 1, wherein the sample accommodating means further comprises a multiple scattering amplification portion that amplifies a number of multiple scattering of the waves emitted to the sample.

4. The optical detection system of claim 1, wherein the means to detect waves detects the existence of impurities in the sample according to detection of the presence of the focused wave.

* * * * *